United States Patent
Tanikawa et al.

(10) Patent No.: US 6,984,742 B2
(45) Date of Patent: Jan. 10, 2006

(54) METHOD FOR PREPARING POLYPRENYL COMPOUNDS

(75) Inventors: Shin Tanikawa, Saitama (JP); Mao Yamashita, Saitama (JP)

(73) Assignee: Nikken Chemicals Co., Ltd., Tokyo (JP)

( * ) Notice: Subject to any disclaimer, the term of this patent is extended or adjusted under 35 U.S.C. 154(b) by 0 days.

(21) Appl. No.: 10/825,096

(22) Filed: Apr. 16, 2004

(65) Prior Publication Data

US 2004/0242690 A1  Dec. 2, 2004

(30) Foreign Application Priority Data

Apr. 18, 2003 (JP) .............................. 2003-114826

(51) Int. Cl.
*C07C 51/00* (2006.01)
(52) U.S. Cl. ..................................................... 554/154
(58) Field of Classification Search ................. 554/154
See application file for complete search history.

(56) References Cited

U.S. PATENT DOCUMENTS 6,369,251 B1    4/2002   Takano et al.

FOREIGN PATENT DOCUMENTS

| JP | 63-32058 | 6/1988 |
| JP | 63-34855 | 7/1988 |

OTHER PUBLICATIONS

English Language Abstract of JP 63-32058.
English Language Abstract of JP 63-34855.
Y. Muto et al., The New England Journal of Medicine, vol. 334, 1996, pp. 1561-1567.
K. Tago et al., J. Chem. Soc. Perkin Trans., vol. 1, 2000, pp. 2073-2078.
W. Still et al., Tetrahedron Letters, vol. 24, 1983, pp. 4405-4408.
T. Kajiwara et al., Agric. Biol. Chem., vol. 45, 1981, pp. 1461-1466.
Chinese Journal of Applied Chemistry, vol. 5, 1988, pp. 70-71.
R. Boden, Synthesis, 1975, p. 784.
G. Bellucci et al., Tetrahedron Letters, vol. 37, 1996, pp. 4225-4228.
M. Mikolajczyk et al., Synthesis, 1975, pp. 278-280.
J. B. Davis et al., J. Chem. Soc. (C), 1966, pp. 2154-2165.
R. Gedye et al., Can. J. Chem., vol. 55, 1977, pp. 1218-1228.
Izv. Akad. Nauk SSSR, Khim, 1990, pp.2544-25550.*
Izv. Akad. Nauk SSSR, Khim, 1988, pp.2382-2385.*
Izv. Akad. Nauk SSSR, Khim, 1988, pp.2377-2382.*

* cited by examiner

*Primary Examiner*—Deborah D. Carr
(74) *Attorney, Agent, or Firm*—Greenblum & Bernstein, P.L.C.

(57) ABSTRACT

A method for preparing a polyprenyl compound wherein an aldehyde represented by the following general formula [I]:

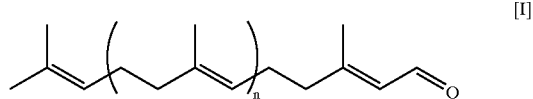

[wherein n represents an integer of from 0 to 3] and a Wittig reagent represented by the following general formula [II]:

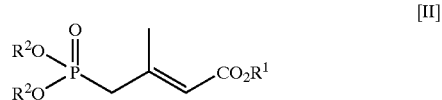

[wherein each of $R^1$ and $R^2$ represents a group consisting of hydrocarbon] are reacted in a medium as a mixture of water and an organic solvent in the presence of a base, and further in the presence of a crown ether. Said method achieves an excellent selectivity and a high yield.

14 Claims, No Drawings

METHOD FOR PREPARING POLYPRENYL COMPOUNDS

TECHNICAL FIELD

The present invention relates to methods for preparing polyprenyl compounds.

BACKGROUND ART (2E,4E,6E,10E)-3,7,11,15-Tetramethyl-2,4,6,10,14-hexadecapentaenoic acid, a class of polyprenyl compound, is known to have an action for activating transcription mediated through retinoic acid receptors as well as an action for inducing differentiation and apoptosis in hepatocellular carcinoma. Clinically, it has been reported that (2E,4E,6E,10E)-3,7,11,15-tetramethyl-2,4,6,10,14-hexadecapentaenoic acid significantly suppressed recurrence after radical cure of hepatoma by long-term administration for one year, indicating an inhibitory action against recurrence of hepatoma, and that almost no side effect is observed such as dysfunction of liver and those with other retinoids (N. Eng. J. Med. 334,1516 (1996)).

As for method for preparing (2E,4E,6E,10E)-3,7,11,15-tetramethyl-2,4,6,10,14-hexadecapentaenoic acid, which is a known compound, the compound is prepared, for example, by using compound A as a synthetic intermediate. The compound A is prepared, for example, by reacting compound B and (2E,6E)-3,7,11-trimethyl-2,6,10-dodecatrien-1-al (for example, see, Japanese Patent Publication (Kohyo) Nos. 63-32058 (1988) and 63-34855 (1988)).

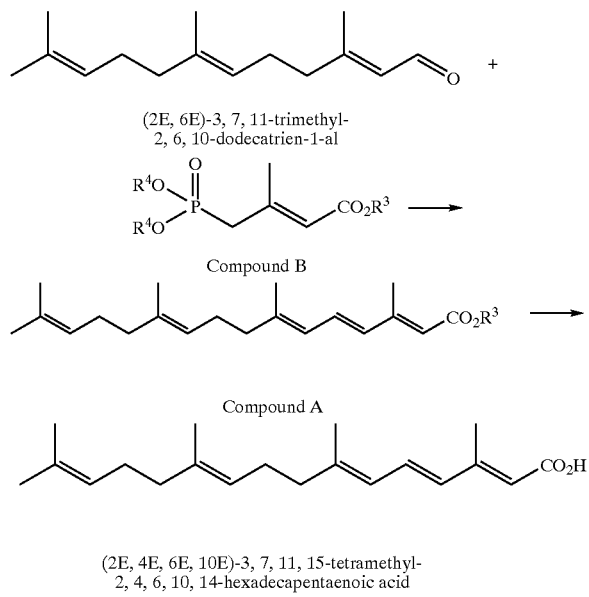

[In the aforementioned general formula, each of $R^3$ and $R^4$ represents an alkyl group.]

However, the above method has disadvantages such as a side production of a large amount of undesired Z-form compounds. Therefore, the development of a method for preparing the E-form compound has been desired which is highly selective and practically applicable.

Generally, as a selective preparation an isomer by using Wittig reaction, a method is known wherein one equivalent or a large excess amount of a crown ether is added to a reaction system (for example, see, J. Chem. Soc., Perkin Trans. 1, 2073 (2000) and Tetrahedron Lett., 24, 4405 (1983)). However, industrial applications of the method are limited because crown ethers are expensive.

A method wherein a catalytic amount of a crown ether is used for selective preparation of an isomer is also reported (for example, see, Agric. Biol. Chem., 45, 1461 (1981), Yingyong Huaxue, 5, 70 (1988), Synthesis, 784 (1975)). However, industrial applications of the method are also limited because the method involves a reaction at a temperature of as low as −40° C. or as high as 80° C. or more, and the method achieves insufficient selectivity.

A method wherein a crown ether is used in a catalytic amount for selective preparation of a styrene derivative is also reported (for example, see, Tetrahedron Lett., 37, 4225 (1996), Synthesis, 278 (1975)). However, the method fails to give a sufficient result of Wittig reaction for an aliphatic aldehyde, or the document neither teaches nor suggests said reaction.

In addition, a method wherein an isomer is selectively prepared by using a catalytic amount of a crown ether and trialkyl-3-methyl-4-phosphonocrotonate as a Wittig reagent (for example, see, Izv. Akad. Nauk SSSR, Khim. 2544 (1990), Izv. Akad. Nauk SSSR, Khim. 2382 (1988), Izv. Akad. Nauk SSSR, Khim. 2377 (1988)). However, industrial applications of the method are limited because the method has a problem of insufficient selectivity.

DISCLOSURE OF THE INVENTION

An object of the present invention is to solve the aforementioned problems and provide a method for preparing a polyprenyl compound which is industrially advantageous.

Under these circumstances, the inventors of the present invention conducted various intensive studies to find an industrially advantageous method for preparing a polyprenyl compound. As a result, they found a novel method for preparing a polyprenyl compound. The present invention was achieved on the basis of this finding.

The present invention thus relates to: (1) a method for preparing a polyprenyl compound represented by the following general formula [III]:

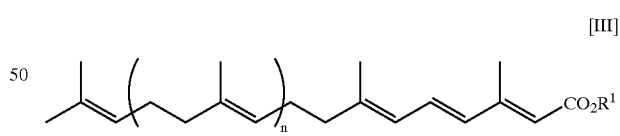

[wherein n represents an integer of from 0 to 3, and $R^1$ represents a group consisting of hydrocarbon]

which is characterized in that an aldehyde represented by the following general formula [I]:

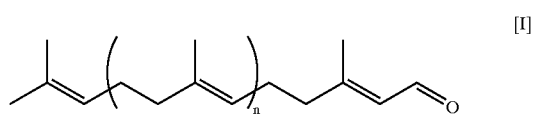

[wherein n has the same meaning as that defined in the aforementioned general formula [III]] and a Wittig reagent represented by the following general formula [II]:

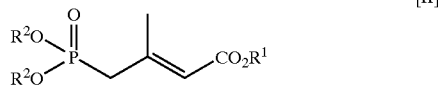

[wherein each of $R^1$ and $R^2$ represents a group consisting of hydrocarbon] are reacted in a medium as a mixture of water and an organic solvent in the presence of a base, and further in the presence of a crown ether.

The present invention also relates to: (2) a method for preparing a polyprenyl compound represented by the following general formula [IV]:

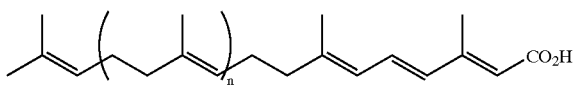

[wherein n has the same meaning as that defined in the aforementioned general formula [III]]

which is characterized in that an aldehyde represented by the aforementioned general formula [I] and a Wittig reagent represented by the aforementioned general formula [II] are reacted in a medium as a mixture of water and an organic solvent in the presence of a base, and further in the presence of a crown ether to obtain the compound represented by the aforementioned general formula [III], and then said compound is subjected to a hydrolysis reaction in the presence of a base.

The present invention preferably relates to: (3) the method according to (1) or (2), wherein the crown ether is 15-crown-5, 18-crown-6, 1-aza-15-crown-5, 1-aza-18-crown-6, benzo-15-crown-5, benzo-18-crown-6, or dibenzo-18-crown-6; more preferably relates to: (4) the method according to (1) or (2), wherein the crown ether is 15-crown-5, 18-crown-6; and most preferably relates to: (5) the method according to (1) or (2), wherein the crown ether is 15-crown-5.

The present invention also preferably relates to: (6) the method according to any one of (1) to (5), wherein the Wittig reagent represented by the aforementioned general formula [II] is triethyl-3-methyl-4-phosphonocrotonate; and (7) the method according to any one of (1) to (6), wherein the aldehyde represented by the aforementioned general formula [I] is (2E,6E)-3,7,11-trimethyl-2,6,10-dodecatrien-1-al.

The method of the present invention can achieve the preparation of (2E,4E,6E,10E)-3,7,11,15-tetramethyl-2,4,6,10,14-hexadecapentaenoic acid in an excellent selectivity and a high yield, and is advantageous for industrial applications.

BEST MODE FOR CARRYING OUT THE INVENTION

In the aforementioned formulas, each of $R^1$ and $R^2$ represents a group consisting of hydrocarbon. As the group consisting of hydrocarbon, an alkyl group, an alkenyl group, an alkynyl group, a cycloalkyl group, a cycloalkenyl group, an aryl group or the like may be used, and an alkyl group is preferably used. As the alkyl group, an alkyl group having 1 to 21 carbon atoms is preferred, which may be linear or branched. As the alkyl group, examples include methyl, ethyl, propyl, isopropyl, n-butyl, sec-butyl, tert-butyl, n-pentyl, neopentyl, 2-methylbutyl, 1-methylbutyl, 1-ethylpropyl, 1,1-dimethylpropyl, n-hexyl, 1-methylpentyl, 2-methylpentyl, 3-methylpentyl, 4-methylpentyl, 3,3-dimethylbutyl, 2,2-dimethylbutyl, 1,1-dimethylbutyl, 2-ethylbutyl, 1-ethylbutyl, 1,3-dimethylbutyl, n-heptyl, 5-methylhexyl, 4-methylhexyl, 3-methylhexyl, 2-methylhexyl, 1-methylhexyl, 3-ethylpentyl, 2-ethylpentyl, 1-ethylpentyl, 4,4-dimethylpentyl, 3,3-dimethylpentyl, 2,2-dimethylpentyl, 1,1-dimethylpentyl, n-octyl, 6-methylheptyl, 5-methylheptyl, 4-methylheptyl, 3-methylheptyl, 2-methylheptyl, 1-methylheptyl, 1-ethylhexyl, 1-propylpentyl, 3-ethylhexyl, 5,5-dimethylhexyl, 4,4-dimethylhexyl, 2,2-diethylbutyl, 3,3-diethylbutyl, and 1-methyl-1-propyl. However, the alkyl groups are not limited to these examples.

In the general formula [III], n represents 0 to 3, preferably 0 to 2, more preferably 1.

As $R^1$, preferred examples include the aforementioned alkyl groups having 1 to 11 carbon atoms, and more preferred examples include methyl group and ethyl group.

As $R^2$, preferred examples include the aforementioned alkyl groups having 1 to 11 carbon atoms, and more preferred examples include methyl group and ethyl group.

Any of the aldehydes represented by the general formula [I] and the Wittig reagents represented by the general formula [II], which are used in the present invention, are known compounds or compounds easily prepared by a known method (for example, J. Chem. Soc. (C), 2154–2165 (1966), Can. J. Chem. 55, 1218(1977) and the like).

The polyprenyl compound represented by the general formula [III] can be prepared by reacting the aldehyde represented by the general formula [I] with the Wittig reagent represented by the general formula [II] in a medium as a mixture of water and an organic solvent, in the presence of a base, and further in the presence of a crown ether.

The aforementioned reaction can be conducted in a mixed solvent of water and an organic solvent such as an ether such as diethylether, diisopropyl ether, tetrahydrofuran, dioxane, dimethoxyethane, 2-methoxyetyl ether, and petroleum ether; an aromatic hydrocarbon such as benzene and toluene; a halogenated hydrocarbon such as dichloromethane, chloroform; an aliphatic hydrocarbon such as hexane, heptane, and octane; aliphatic cyclic hydrocarbon such as cyclohexane; or a mixture thereof. A mixed solvent of water and an aromatic hydrocarbon such as benzene and toluene may be preferably used. A reaction temperature may be from −20° C. to about 100° C., preferably from 5° C. to 30° C. Period of time for the reaction may be varied depending on reaction conditions, and is generally from 1 to 24 hours.

Examples of the crown ether include 15-crown-5, 18-crown-6, 1-aza-15-crown-5, 1-aza-18-crown-6, benzo-15-crown-5, benzo-18-crown-6, and dibenzo-18-crown-6, preferably 5-crown-5 and 18-crown-6, and more preferably 15-crown-5. The crown ether may be used less than a stoichiometric amount, preferably in an amount of 0.01 to 0.90 molar equivalents, more preferably 0.05 to 0.20 molar equivalents, and most preferably 0.1 molar equivalents.

Examples of the base used for the aforementioned reaction include hydroxides of alkali metals such as lithium hydroxide, sodium hydroxide, potassium hydroxide, and barium hydroxide, preferably sodium hydroxide and potassium hydroxide, more preferably sodium hydroxide. An amount of the base used for the reaction may be about 10 to 15 molar equivalents.

The polyprenyl compound of the present invention which is represented by the general formula [IV] can be prepared by subjecting the polyprenyl compound represented by the general formula [III] to a hydrolysis reaction in the presence of a base.

The aforementioned reaction can be conducted in a mixed solvent of water and an organic solvent such as an alcohol such as methanol, ethanol, 1-propanol, 2-propanol, 1-butanol, 2-butanol, 3-methylpropanol, and 3-methyl-1-butanol; an ether such as tetrahydrofuran; or a mixture thereof. Preferably, an alcohol such as methanol, ethanol, 1-propanol, 2-propanol, 1-butanol, 2-butanol, 3-methylpropanol, and 3-methyl-1-butanol is used. A reaction temperature may be from 0° C. to about the boiling point of a solvent used, preferably from 5° C. to 100° C. Period of time for the reaction may be varied depending on reaction conditions, and is generally 1 to 24 hours.

Examples of the base used for the aforementioned reaction include hydroxides of alkali metal such as lithium hydroxide, sodium hydroxide, potassium hydroxide, and barium hydroxide, preferably sodium hydroxide and potassium hydroxide. An amount of the base used for the reaction is about 1 to 10 molar equivalents, and preferably 1 to 3 molar equivalents.

The reaction product can be isolated and purified by an appropriate combination of ordinary means such as centrifugation, concentration, separation, washing, drying, recrystallization, distillation, and column chromatography.

EXAMPLES

The present invention will be more specifically explained with reference to the following examples and reference examples. However, the scope of the present invention is not limited to these examples.

Example 1

Preparation of ethyl (2E,4E,6E,10E)-3,7,11,15-tetramethyl-2,4,6,10,14-hexadecapentaenoate 15-crown-5 (0.5 g, 0.1 equivalents, 2.27 mmol) was dissolved in 30 ml of toluene at room temperature, and added with 20 ml of 50% aqueous sodium hydroxide solution. To the solution, triethyl-3-methyl-4-phosphonocrotonate (7.87 g, 1.05 equivalents, 23.8 mmol) and then 5 ml toluene solution of farnesal (5.0 g, 22.7 ml) were added with stirring at 0° C. The mixture was stirred at room temperature for one hour. The organic and aqueous layers were separated, and the organic layer was washed with saturated ammonium chloride solution and saturated brine, and dried over magnesium sulfate. The solvent was evaporated under reduced pressure. The residue was purified by silica gel column chromatography to obtain 7.4 g of the title compound (yield 98%, 2E:2Z=>99:1) as a yellow oil.

$^1$H-NMR(CDCl$_3$) δ (ppm); 1.29(3H, t, J=7.1 Hz), 1.60 (3H, s), 1.61(3H, s), 1.68(3H, s), 1.85(3H, s), 1.90–2.18 (8H, m), 2.33 (3H, s), 4.17(2H, q, J=7.1 Hz), 5.02–5.18 (2H, m), 5.74 (1H, s), 5.97 (1H, d, J=11.2 Hz), 6.17(1H, d, J=15.1 Hz), 6.84(1H, dd, J=11.2, 15.1 Hz)

Example 2

Preparation of (2E,4E,6E,10E)-3,7,11,15-tetramethyl-2,4,6,10,14-hexadecapentaenoic acid Potassium hydroxide (3.0 g) was dissolved in 20 ml of 2-propanol at 100° C. The solution was added with 2-propanol (10 ml) solution of ethyl (2E,4E,6E,10E)-3,7,11,15-tetramethyl-2,4,6,10,14-hexadecapentaenoate obtained in Example 1, and stirred at the same temperature for 5 minutes. The reaction mixture was added to ice-water and washed with n-hexane. The solution was neutralized with 10% hydrochloric acid and extracted with n-hexane. The resulting organic layer was washed with saturated brine and dried over magnesium sulfate. The solvent was evaporated under reduced pressure. The residue was recrystallized from methanol to obtain 3.5 g of the title compound (yield 51%) as a yellow crystal.

$^1$H-NMR(CDCl$_3$) δ (ppm); 1.60(3H, s), 1.61(3H, s), 1.68 (3H, s), 1.86(3H, s), 1.96–2.09 (4H, m), 2.15 (2H, s), 2.16 (2H, s), 2.34 (3H, s), 5.06–5.10 (2H, m), 5.77 (1H, s), 5.98(1H, d, J=11.2 Hz), 6.20(1H, d, J=15.1 Hz), 6.90(1H, dd, J=11.2, 15.1 Hz), 11.8(1H, brs)

Example 3

Preparation of ethyl(2E,4E,6E)-3,7,11-trimethyl-2,4,6,10-dodecatetraenoate 15-crown-5 (0.9 g, 0.1 equivalents, 4.0 mmol) was dissolved in 50 ml of toluene at room temperature, and added with 32 ml of 50% aqueous sodium hydroxide solution. To the solution, triethyl-3-methyl-4-phosphonocrotonate (11.1 g, 1.05 equivalents, 42 mmol) and then 7 ml toluene solution of geranial (6.1 g, 40 mmol) were added under stirring at 0° C. The mixture was stirred at room temperature for 1.5 hours. The organic and aqueous layers were separated, and the organic layer was washed with saturated ammonium chloride solution and saturated brine, and dried over magnesium sulfate. The solvent was evaporated under reduced pressure. The residue was purified by silica gel column chromatography to obtain 9.2 g of the title compound (yield 87%, 2E:2Z=93:7) as a yellow oil.

$^1$H-NMR(CDCl$_3$) δ (ppm); 1.29(3H, t, J=7.1 Hz), 1.61 (3H, s), 1.69(3H, s), 1.85(3H, s), 2.10–2.21 (4H, m), 2.33 (3H, s), 4.17(2H, q, J=7.1 Hz), 5.09 (1H, brs), 5.74 (1H, s), 5.97 (1H, d, J=11.0 Hz), 6.18(1H, d, J=15.1 Hz), 6.83(1H, dd, J=11.0, 15.1 Hz)

Example 4

Preparation of (2E,4E,6E)-3,7,11-trimethyl-2,4,6,10-dodecatetraenoic acid

Potassium hydroxide (3.0 g) was dissolved in 30 ml of 2-propanol at 100° C. The solution was added with 2-propanol solution (10 ml) of ethyl (2E,4E,6E)-3,7,11-trimethyl-2,4,6,10-dodecatetraenoate obtained in Example 3 (9.1 g, 34.5 mmol), and stirred at the same temperature for 15 minutes. The reaction mixture was added to ice-water and washed with n-hexane. The solution was neutralized with 10% hydrochloric acid and extracted with n-hexane. The resulting organic layer was washed with saturated brine and dried over magnesium sulfate. The solvent was evaporated under reduced pressure. The residue was recrystallized from methanol twice to obtain 1.5 g of the title compound (yield 18%) as a yellow crystal.

$^1$H-NMR(CDCl$_3$) δ (ppm); 1.61(3H, s), 1.69(3H, s), 1.85 (3H, s), 2.10–2.19 (4H, m), 2.34 (3H, d, J=1.0 Hz), 5.09 (1H, brs), 5.77 (1H, s), 5.98(1H, d, J=11.0 Hz), 6.21(1H, d, J=15.1 Hz), 6.90(1H, dd, J=11.0, 15.1 Hz), 11.6(1H, brs)

Reference Example 1

Preparation of ethyl(2E,4E,6E,10E)-3,7,11,15-tetramethyl-2,4,6,10,14-hexadecapentaenoate Under argon atmosphere, sodium ethoxide (2.16 g, 1.26 equivalents) was suspended in 20 ml of dimethylformamide, and the suspension was added dropwise with 5 ml dimethylformamide solution of triethyl-3-methyl-4-phosphonocrotonate (7.87 g, 1.2 equivalents, 23.28 mmol) at room temperature. The reaction mixture was then added dropwise with 5 ml dimethylformamide solution of farnesal (5.0 g, 22.7 ml) under stirring at −10° C., and further stirred at the same temperature for 30 minutes. The reaction mixture was added to ice-water. The solution was neutralized with acetic acid and extracted with n-heptane. The resulting organic layer was washed with saturated brine and dried over magnesium sulfate. The solvent was evaporated under reduced pressure. The residue was purified by silica gel column chromatography to obtain 6.6 g of the title compound (yield 88%, 2E:2Z=86:14) as a yellow oil.

The present disclosure relates to subject matter contained in Japanese Patent Application No. 2003-114826, filed on Apr. 18, 2003, the contents of which are herein expressly incorporated by reference in its entirety.

What is claimed is:

1. A method for preparing a polyprenyl compound represented by the following general formula [III]:

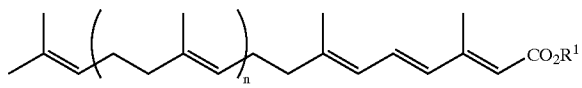
[III]

[wherein n represents an integer of from 0 to 3, and R$^1$ represents a group consisting of hydrocarbon] which is characterized in that an aldehyde represented by the following general formula [I]:

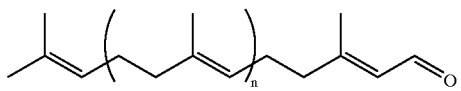
[I]

[wherein n has the same meaning as defined in [III]] and a Wittig reagent represented by the following general formula [II]:

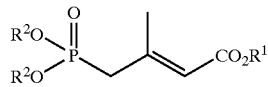
[II]

[wherein each of R$^1$ and R$^2$ represents a group consisting of hydrocarbon] are reacted in a medium as a mixture of water and an organic solvent in the presence of a base, and further in the presence of a crown ether.

2. A method for preparing a polyprenyl compound represented by the following general formula [IV]:

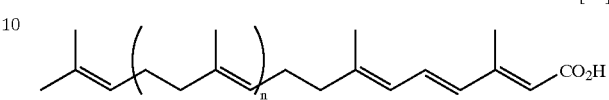
[IV]

[wherein n has the same meaning as that defined in the aforementioned general formula [III]]
which is characterized in that the aldehyde represented by the aforementioned general formula [I] and the Wittig reagent represented by the aforementioned general formula [II] are reacted in a medium as a mixture of water and an organic solvent in the presence of a base, and further in the presence of a crown ether to obtain the compound represented by the aforementioned general formula [III], and then the compound represented by the aforementioned general formula [III] is subjected to a hydrolysis reaction in the presence of a base.

3. The method according to claim 1, wherein the crown ether is 15-crown-5, 18-crown-6, 1-aza-15-crown-5, 1-aza-18-crown-6, benzo-15-crown-5, benzo-18-crown-6, or dibenzo-18-crown-6.

4. The method according to claim 1, wherein the crown ether is 15-crown-5,18-crown-6.

5. The method according to claim 1, wherein the crown ether is 15-crown-5.

6. The method according to claim 1, wherein the Wittig reagent represented by [II] is triethyl-3-methyl-4-phosphonocrotonate.

7. The method according to claim 1, wherein the aldehyde represented by [I] is (2E,6E)-3,7,11-trimethyl-2,6,10-dodecatrien-1-al.

8. The method according to claim 1, wherein the crown ether is 15-crown-5,18-crown-6 and the aldehyde represented by [I] is (2E,6E)-3,7,11-trimethyl-2,6,10-dodecatrien-1-al.

9. The method according to claim 2, wherein the crown ether is 15-crown-5,18-crown-6, 1-aza-15-crown-5, 1-aza-18-crown-6, benzo-15-crown-5, benzo-18-crown-6, or dibenzo-18-crown-6.

10. The method according to claim 2, wherein the crown ether is 15-crown-5,18-crown-6.

11. The method according to claim 2, wherein the crown ether is 15-crown-5.

12. The method according to claim 2, wherein the Wittig reagent represented by [II] is triethyl-3-methyl-4-phosphonocrotonate.

13. The method according to claim 2, wherein the aldehyde represented by [I] is (2E,6E)-3,7,11-trimethyl-2,6,10-dodecatrien-1-al.

14. The method according to claim 2, wherein the crown ether is 15-crown-5, 18-crown-6 and the aldehyde represented by [I] is (2E,6E)-3,7,11-trimethyl-2,6,10-dodecatrien-1-al.

* * * * *